(12) United States Patent
Beard

(10) Patent No.: US 9,138,169 B2
(45) Date of Patent: Sep. 22, 2015

(54) OXYGEN FACEMASK WITH CAPNOGRAPHY MONITORING PORTS

(75) Inventor: John W. Beard, Lafayette, CA (US)

(73) Assignee: Monitor Mask Inc., Seattle, WA (US)

( * ) Notice: Subject to any disclaimer, the term of this patent is extended or adjusted under 35 U.S.C. 154(b) by 98 days.

(21) Appl. No.: 13/227,345

(22) Filed: Sep. 7, 2011

(65) Prior Publication Data

US 2013/0060157 A1  Mar. 7, 2013

(51) Int. Cl.
| | | |
|---|---|---|
| *A61B 5/08* | (2006.01) | |
| *A61B 5/097* | (2006.01) | |
| *A61M 16/06* | (2006.01) | |
| *A61B 5/083* | (2006.01) | |
| *A61M 16/08* | (2006.01) | |
| *A61M 16/20* | (2006.01) | |
| *A61M 16/10* | (2006.01) | |

(52) U.S. Cl.
CPC ............. *A61B 5/097* (2013.01); *A61B 5/0836* (2013.01); *A61M 16/06* (2013.01); *A61M 16/085* (2014.02); *A61M 16/208* (2013.01); *A61M 2016/1025* (2013.01); *A61M 2202/0208* (2013.01); *A61M 2209/06* (2013.01); *A61M 2230/435* (2013.01)

(58) Field of Classification Search
CPC ..... A61M 16/00; A61M 16/06; A61M 16/08; A61M 16/085; A61M 16/208; A61M 2230/435; A61M 2202/0208; A61M 2016/1025; A62B 7/00; A61B 5/0836; A61B 5/097
USPC ............. 128/201.22–201.25, 201.28, 203.29, 128/204.22, 204.23, 205.12, 205.25, 128/205.28; 600/529–543
See application file for complete search history.

(56) References Cited

U.S. PATENT DOCUMENTS

| | | | |
|---|---|---|---|
| 4,201,205 A | | 5/1980 | Bartholomew |
| 4,265,239 A | | 5/1981 | Fischer, Jr. et al. |
| 4,475,559 A | * | 10/1984 | Horn .............................. 600/529 |
| 5,400,781 A | | 3/1995 | Davenport |
| 5,431,158 A | | 7/1995 | Tirotta |
| 5,474,060 A | * | 12/1995 | Evans ....................... 128/204.22 |
| 5,488,944 A | | 2/1996 | Kennedy |
| 5,586,551 A | | 12/1996 | Hilliard |
| 5,857,460 A | | 1/1999 | Popitz |
| 6,017,315 A | * | 1/2000 | Starr et al. .................... 600/538 |
| 6,247,470 B1 | | 6/2001 | Ketchedjian |
| 6,263,874 B1 | | 7/2001 | LeDez et al. |

(Continued)

FOREIGN PATENT DOCUMENTS

| | | |
|---|---|---|
| EP | 1 027 905 A2 | 8/2000 |
| WO | WO 91/14469 A1 | 10/1991 |
| WO | WO 2008/153830 A1 | 12/2008 |

OTHER PUBLICATIONS

Dispo-Med; Capno Mask; Product detail; retrieved from internet on Jan. 11, 2013; http://www.alibaba.com/product-free/105806739/Dispo_Med_Capno_mask/showimage.html; 2 pages total; date of publication unknown; this web address was available to applicant(s) at least as of Jun. 8, 2011.

(Continued)

*Primary Examiner* — Navin Nathnithithadha
*Assistant Examiner* — Eric Messersmith
(74) *Attorney, Agent, or Firm* — Seed IP Law Group PLLC

(57) ABSTRACT

An oxygen face mask to cover a user's nose and at least partially cover a user's mouth with lateral sampling ports; systems including such a face mask; and methods of using such a face mask.

8 Claims, 6 Drawing Sheets

(56) References Cited

U.S. PATENT DOCUMENTS

| | | | |
|---|---|---|---|
| 6,379,312 B2 | 4/2002 | O'Toole | |
| 6,386,198 B1* | 5/2002 | Rugless | 128/206.21 |
| 6,439,234 B1 | 8/2002 | Curti et al. | |
| 7,004,168 B2 | 2/2006 | Mace et al. | |
| 7,146,980 B2 | 12/2006 | Loncar | |
| 7,152,604 B2 | 12/2006 | Hickle et al. | |
| 7,305,988 B2 | 12/2007 | Acker et al. | |
| 7,607,433 B2 | 10/2009 | Silva et al. | |
| 7,621,272 B2 | 11/2009 | Orr | |
| 8,365,734 B1* | 2/2013 | Lehman | 128/206.28 |
| 8,960,195 B2* | 2/2015 | Lehman | 128/206.28 |
| 2005/0257791 A1* | 11/2005 | Biederman | 128/204.23 |
| 2006/0196510 A1 | 9/2006 | McDonald et al. | |
| 2007/0023040 A1 | 2/2007 | Nashed | |
| 2008/0053449 A1 | 3/2008 | Lindblom et al. | |
| 2011/0100368 A1 | 5/2011 | Taylor-Kennedy | |
| 2011/0203591 A1 | 8/2011 | Amarasinghe | |
| 2012/0216806 A1* | 8/2012 | Rookard et al. | 128/203.29 |

OTHER PUBLICATIONS

Galemed; Product detail; retrieved from the internet on Jan. 30, 2013; http://www.galemed.com/main/Products/ProductDetail.asp?ID=629&ProdID=3076; 1 page; date of publication unknown; this web address was available to applicant(s) at least as of Jun. 8, 2011.

Intersurgical; Sentri ETCO2 maks; Product detail; retrieved from internet on Jan. 11, 2013; http://www.intersurgical.com/info/sentri; 2 pages total; date of publication unknown; this web address was available to applicant(s) at least as of Jun. 8, 2011.

Kassil et al.; Raspiratomaya podderzhka; Rukovodstvo dlya vrachei; Meditsina; p. 290; last paragraph; (the year of publication is sufficiently earlier than the effective U.S. filing date and any foreign priority date) 1997 (submitted with a copy of ISR).

Mediplus; Capnomask; Product detail; retrieved from internet on Jan. 11, 2013; http://www.mediplus.co.uk/c-Capnomask_39; 2 pages total; date of publication unknown; this web address was available to applicant(s) at least as of Jun. 8, 2011.

Penlon America; Capnography Oxygen Masks; Product detail; retrieved from internet on Jun. 22, 2011; 1 page total; https://www.penlonamerica.com/products/capnography_oxygen_masks_2.htm; date of publication unknown; this web address was available to applicant(s) at least as of Jun. 8, 2011.

Respan; Jemsdal R Mask; Respan Respiratory Products; retrieved from internet on Jan. 11, 2013; 1 page; http://www.respan.com/pages/jemsdal.html; date of publication unknown; this web address was available to applicant(s) at least as of Jun. 8, 2011.

Rukovodstvo po anesteziologii; Editors Eitkenkheda et al.; Meditsina; Moscow; vol. 1; p. 456; col. 2; par. 3; (the year of publication is sufficiently earlier than the effective U.S. filing date and any foreign priority date) 1999 (submitted with a ISR).

Southmedic; Capnoxygen R; Not just another oxygen mask; Product detail; retrieved from internet on Jan. 11, 2013; http://www.southmedic.com/products/capnoxygen.php; 4 pages total; date of publication unknown; this web address was available to applicant(s) at least as of Jun. 8, 2011.

* cited by examiner

OXYGEN FACEMASK WITH CAPNOGRAPHY MONITORING PORTS

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to oxygen delivering facemasks, systems including such oxygen delivering facemasks, and methods of using such facemasks and systems.

BACKGROUND

A steady inflow of oxygen is required to sustain human life. A short interruption or reduction in a person's oxygen supply can rapidly lead to brain or body damage, or death. An individual with too little oxygen in his blood (hypoxemia) or at risk for developing hypoxemia may be given oxygen. An individual able to breathe on his own may be given supplemental oxygen therapy for various reasons and in various places. Oxygen may be given to an individual who has shortness of breath or COPD (chronic obstructive pulmonary disease). Supplemental oxygen may be delivered to a patient who has suffered trauma or an acute myocardial infarction (heart attack). Supplemental oxygen may be given during certain surgical interventions or during post-anesthesia recovery after a surgical intervention. Supplemental oxygen may be given anywhere. It may be given, for example, in a person's home, in a clinic or in a hospital such as in a trauma center, an emergency room, an operating room, a recovery room, or an intensive care unit. A person who is receiving supplemental oxygen therapy is generally weak, injured, or compromised in some way. Such a person is prone to stop breathing briefly or altogether. In order to determine if a person receiving supplemental oxygen is continuing to breathe, an assay may be performed. A non-invasive, expiratory gas sampling device may be used to determine if the person is exhaling as evidence he is continuing to breathe. Commonly, the expiratory gas sampled is carbon dioxide.

Both facemasks and nasal cannula have been used to deliver supplemental oxygen and to sample carbon dioxide. U.S. Pat. No. 5,400,781 to Davenport discloses an oxygen mask with two openings in the floor of the chamber in front of the mouth that lead to an oxygen source and a carbon dioxide monitor. U.S. Pat. No. 5,474,060 to Evans describes an oxygen mask with an inlet for directing a flow of gas (oxygen) to the interior of the mask, and a port for allowing the exhaled air to flow through and a tube for directing the exhaled air to a monitoring apparatus. U.S. Pat. No. 6,247,470 to Ketchedjian uses a flexible lever arm near the face and connected to tubing to deliver oxygen and sample exhaled gases. U.S. Pat. No. 6,439,234 to Curti describes a nasal cannula with two prongs, with the first prong for delivering oxygen and the second prong for sampling carbon dioxide. WO 91/14469 teaches a nasal gas cannula and an oral gas capture member for delivering and capturing carbon dioxide.

Although these facemasks and cannulas attempt to solve some of the problems with delivering oxygen to an individual and determining if he is breathing, none provides an easy to use, universal device that can deliver oxygen and sample an expiratory gas in a variety of circumstances. The present invention is directed to meeting these, as well as other, needs.

SUMMARY OF THE DISCLOSURE

Described herein are devices, methods, systems, and kits useful for administering and sampling gases from a mammalian body. The devices are particularly useful for administering oxygen and sampling carbon dioxide, though they may be used as a part of any appropriate treatment procedure.

One aspect of the invention provides a face mask to cover a user's nose and at least partially cover a user's mouth. In some embodiments, the face mask includes two or more lateral ports on opposing sides of a midline of the mask and is configured to deliver oxygen to a user. In some embodiments, the face mask includes an oxygen inlet port having a center, and at least one of the sampling ports is at least about 20 mm away from the center of the oxygen inlet port. In some embodiments, the face mask includes a conduit coupled to a sampling port on only one side of the mask.

In some embodiments, the face mask includes at least one vent configured to release gas from the mask. In some embodiments the vent has a vent center and a center of the sampling port is within about 15 mm of the vent center. In some embodiments, the face mask includes a plurality of vents and the plurality of vents is arranged around one of the sampling ports.

In some embodiments, the face mask includes a mask reservoir portion for containing a pocket of gas and a lateral sampling port is in the mask reservoir portion. In some embodiments, the face mask is configured to removably connect with a user's face to create a mask sealing portion configured to retain gas in the mask.

Another aspect of the invention provides a breathing mask system including a face mask and a sensor and the facemask includes at least two lateral sampling ports on opposing sides of a midline of the mask. The breathing mask may be configured to cover a user's nose and at least partially cover a user's mouth. The sensor may be coupled to a lateral port. In some embodiments, the sensor is configured to detect an expiratory gas. In some embodiments, the system may include an alarm configured to provide a signal when a level of an expiratory gas detected by the sensor is different from a threshold amount. In some embodiments, the sensor is configured to detect a carbon dioxide pressure (e.g. a carbon dioxide partial pressure). In some embodiments, the face mask may include an oxygen inlet port.

Another aspect of the invention provides a method of using an oxygen face mask having at least two lateral sampling ports on opposing sides of a midline of the mask to sample an expiratory gas, the method including the steps of choosing one lateral sampling port; and coupling a conduit with the port. In some embodiments, the method includes the additional step of coupling an expiratory gas sensor to the conduit. In some embodiments, the expiratory gas sensor is configured to assay carbon dioxide and the method includes the step of assaying a partial pressure of carbon dioxide.

In some embodiments, the method includes the step of venting expiratory gas through a vent in the mask. In some embodiments, the method includes the step of administering at least one of a nebulizer treatment and an aerosol treatment. In some embodiments, the method includes the step of providing at least about 60% oxygen. In some embodiments, the method includes expelling expiratory gas through a one-way valve.

Another aspect of the invention provides a kit including a face mask having at least two lateral sampling ports on opposing sides of a midline of the mask. The mask may be configured to provide oxygen. In some embodiments, the kit may additionally include one or more instruction for use, a sampling conduit, a sensor, an oxygen conduit, a rebreather reservoir, and a one way valve.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
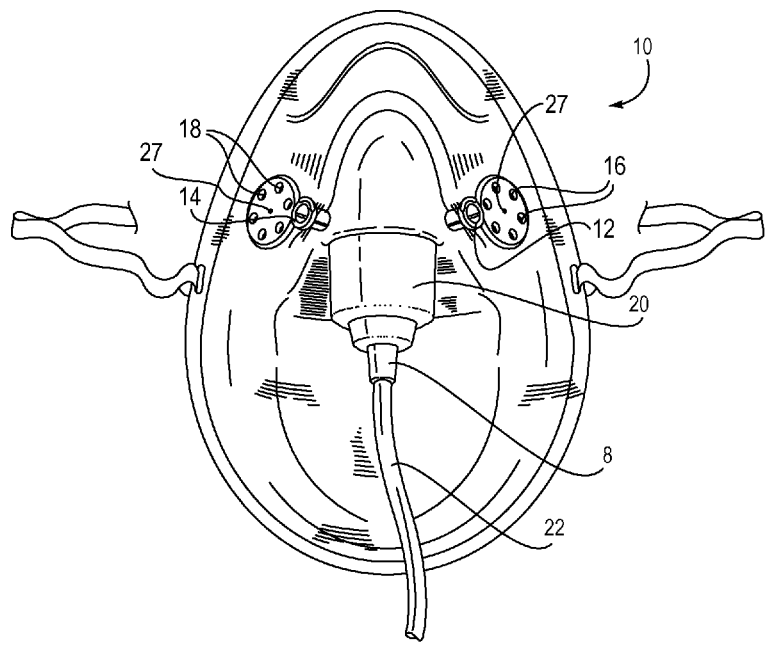
FIG. 1A is a front view of an oxygen facemask with lateral sampling ports according to one aspect of the disclosure.

The present invention includes a universal oxygen facemask for delivering oxygen and sampling a respiratory gas for use in a variety of clinical scenarios for an individual able to breathe on his own, but requiring some supplemental oxygen. Respiratory gas (e.g. carbon dioxide) may be monitored using the mask to ensure that the individual continues to breathe. Ensuring that the individual is breathing may be especially important when an individual is under sedation or has recently experienced a status change such as a surgical procedure or trauma. The mask may have two (or more) lateral sampling ports for sampling a respiratory gas. The ports may be located between a level of the nose and a level of the mouth when the mask is in use. FIG. 1 (front view) and FIG. 2 (side view) show mask 10 embodying features of the invention including left lateral sampling port 12 and right lateral sampling port 14. Having two lateral sampling ports makes the mask easier to use and allows for better samples to be taken. This may be the case even though, in practice, a sample may be taken from only one of the ports. The second (or additional) lateral port may be unused. A mask with two lateral sampling ports allows the mask to be used in nearly all clinical scenarios; mask manufacturing can be streamlined and the best mask for almost any situation is readily available. A mask with at least two lateral sampling ports eliminates the need to have a series of different masks for different purposes. A mask having two lateral sampling ports may be the standard for use with all patients, and the use of interchangeable components coupled with the mask for specific clinical scenarios may be the care path.

The facemask of the invention can be used for a variety of clinical purposes in a variety of settings. The facemask can be used while the person needing oxygen is supine, lateral or prone; while the person's face is covered with a drape; during nebulizer therapy; or during use of a non-rebreather mask; during use of an oxygen calibration device (e.g. a Venturi device); and/or during high flow oxygen therapy. In addition, the mask could be used for administering oxygen and monitoring an aspect(s) of respiratory physiology, such as end tidal $CO_2$ and respiratory rate during a test of athletic endurance or cardiovascular health.

Ports high on the mask and lateral to the midline of the mask are more accessible compared with the location of ports on masks in the prior art. The lateral ports are easy to access in order to attach a sampling conduit (e.g. tubing) in a variety of patient positions and patient-caregiver physical arrangements. If a monitoring port is low on the mask, as with prior art masks, it is difficult to gain access to the port. First, accessing the port in the prior art masks is challenging due to the port's immediate proximity to the oxygen port and the small space available to manipulate (e.g. attach and detach) a conduit. This could be of particular importance in a small pediatric mask. Secondly, a port located near the oxygen inflow is out of view and cumbersome to reach in the most common operating room scenario, for which the anesthesia provider is positioned at the head of the patient's bed. Any difficulty in accessing the monitoring port is magnified in challenging clinical situations such as an obese, prone, or laterally positioned patient. Additionally, the patient's neck, chin or other body part may get in the way of monitoring port access, especially in the case in which a patient is lying on his side.

Figure 1B:
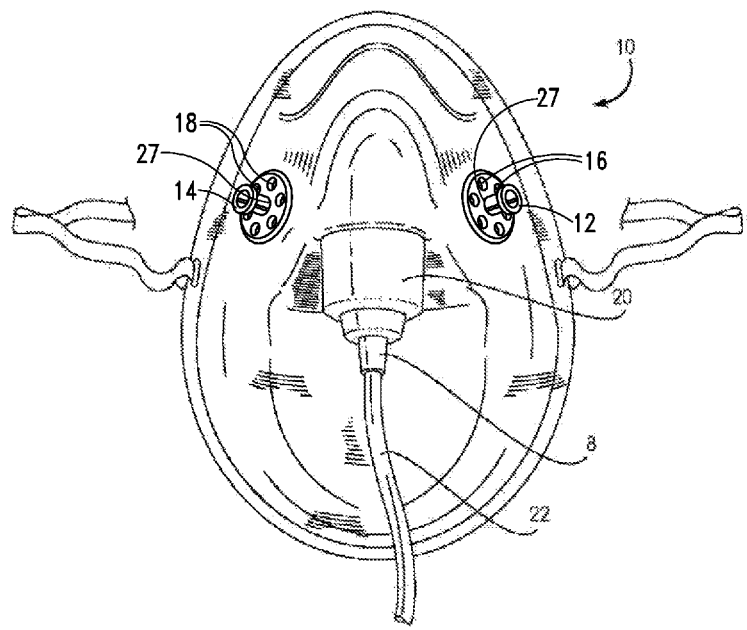
FIG. 1B is a front view of an oxygen facemask with lateral sampling ports at the center of the respective vents.
Figure 2:
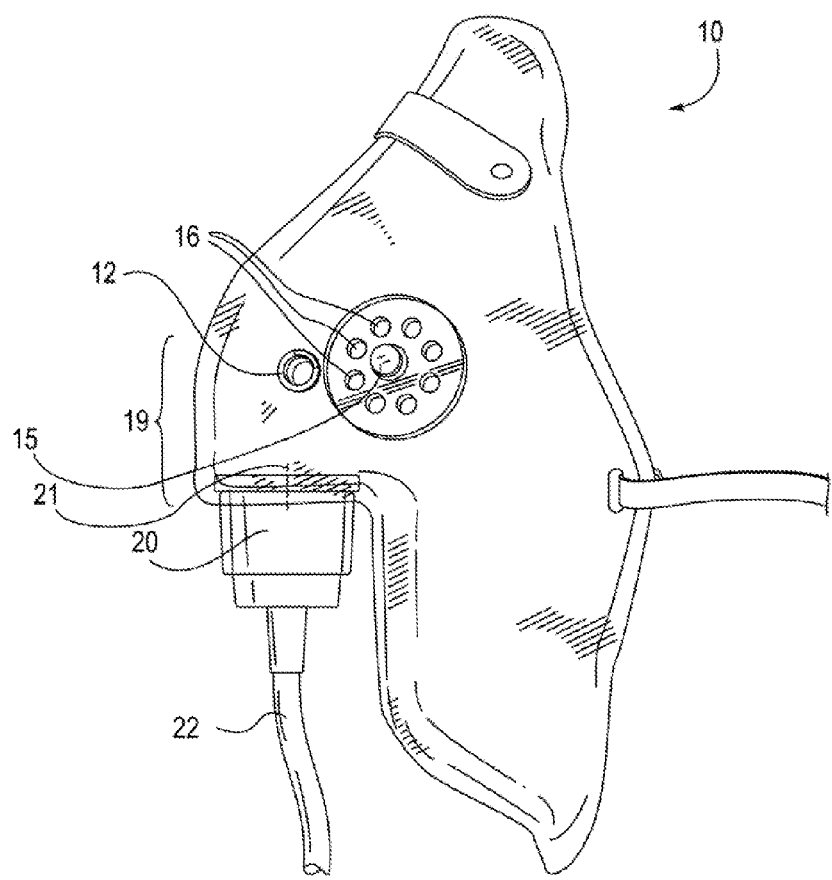
FIG. 2 is a side view of a facemask with a lateral monitoring port according to one embodiment.

The mask design of the disclosure also achieves the aims of separating the port from the other equipment and from other lines (e.g. the oxygen input port, oxygen conduit, or oxygen bag). This separation prevents the sampling port from interfering with other equipment and lines as well as preventing the other equipment and lines from interfering with sampling port access and sampling conduit access. This design also avoids unnecessary stimulation of the patient by keeping lines and monitors away from the eyes and other sensitive parts of the face. FIGS. 1 and 2 depict left, right lateral sampling ports 12, 14 positioned away from the oxygen inlet port center 21 of oxygen line inlet port 20 on mask 10, and out of the way of oxygen conduit coupler 8, shown coupling oxygen inlet port 20 with oxygen conduit 22. In one example, a center of the lateral sampling port is at least about 20 mm away from oxygen inlet port center 21 of oxygen inlet port 20.

Having two sampling ports available allows a care provider (e.g. a physician, nurse, or other person) to choose a convenient sampling port. For example, when a patient is lying supine while undergoing a surgical procedure, the care provider performing the respiratory gas monitoring often sits at the patient's head. It is easier for the care provider to access one of the lateral ports and connect a tube or conduit to it for monitoring respiratory gas than it is to access a port that is obscured by the patient's neck and may be underneath the oxygen inlet port/oxygen conduit. Depending on various factors, one specific lateral sampling port may be a better choice for the care provider to use. Ease of attachment may be based on the positions of the care provider and/or the monitoring equipment to the patient. For example, a lateral side port can be chosen and easily and directly accessed based on ergonomic considerations such as patient position, monitor position, and caregiver position and handedness. The care provider does not need to reach across the patient's face. As a patient may be conscious during a procedure when wearing an oxygen face mask, this is important. Having a hand close to the eyes creates or worsens a feeling of confinement or claustrophobia in a patient, which are common complaints from oxygen mask users.

Having at least two ports on the mask also means that if one of the ports cannot be used, a second monitoring port is still available. This may be the case, for example, when an individual is lying on his side, such as when a surgical procedure is being performed on the other side, and one of the ports is blocked.

In another example, the mask may be used (e.g. to deliver oxygen) without using the sampling ports to obtain a sample. In another example, samples could be removed from two (or more) sampling ports.

Figure 3:
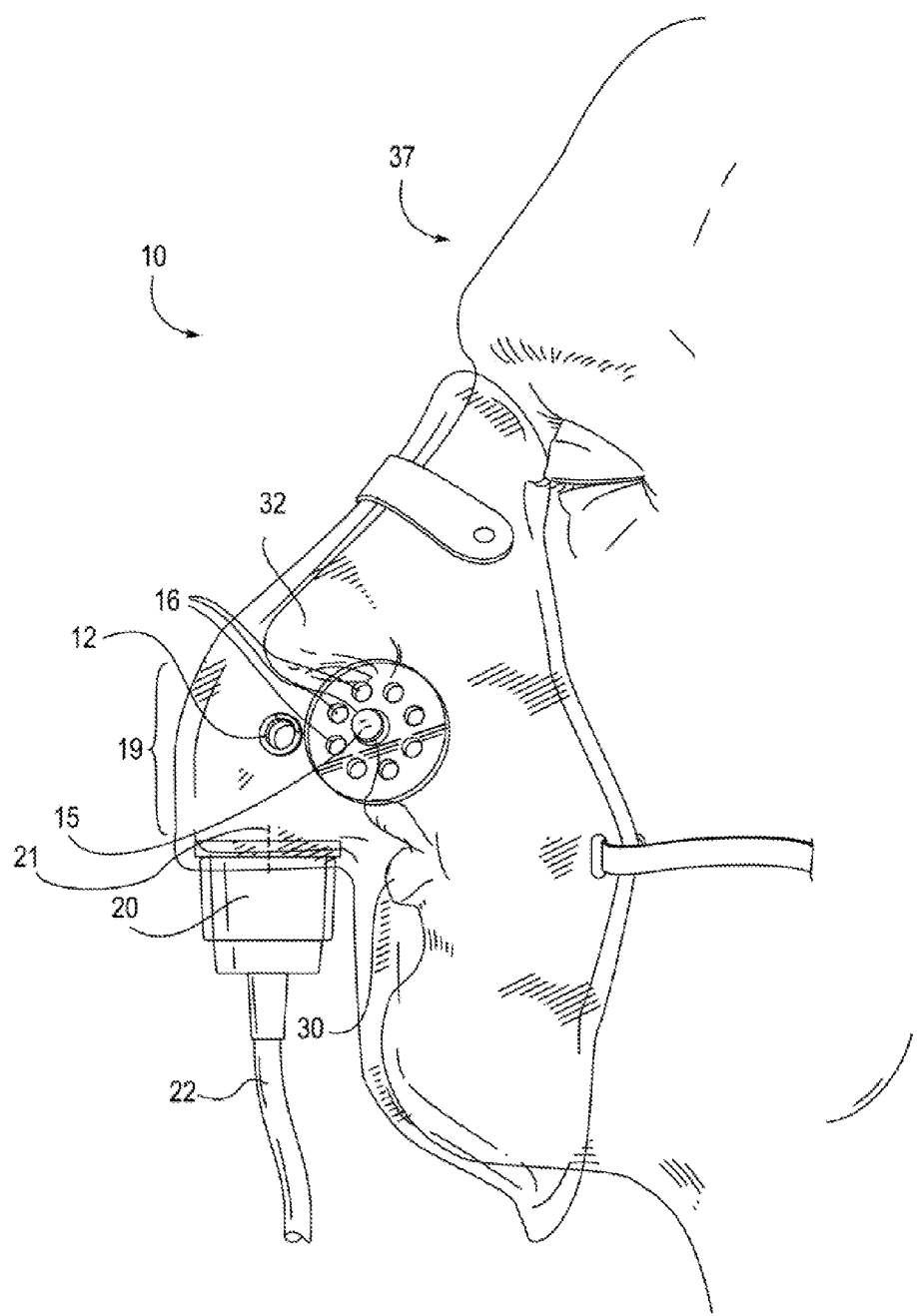
FIG. 3 is a side view of a facemask such as the one shown in FIGS. 1 and 2 in use on a patient.

The ports may be located laterally to the midline of the mask (e.g. on opposing sides of the midline). The ports may be between a level of the nose and a level of the mouth when the mask is in use. In one example, the ports are at or below the bottom of the nose (e.g. below about a level of the nares). In another example, the sampling ports are above the level of the lower lip. In another example, the sampling ports are above the level of the upper lip. The sampling ports may be positioned in any lateral position relative to the nose and mouth. The ports may collect nasal gases, oral gases, or both. The ports may collect other gases (e.g. supplemental oxygen, room air). FIG. 3 shows a side view of patient 37 wearing mask 10 as described herein. Left lateral sampling port 12 is at a level between mouth 30 and nose 32.

The mask may have one or more exhalation vents (e.g. exhalation ports). FIGS. 1-3 show left, right exhalation vents 16, 18. An exhalation vent(s) may release or vent gas and other substance(s) from inside to outside the mask. The gas may be an expiratory gas (e.g. carbon dioxide or oxygen). Although called an exhalation vent(s), the vent may additionally allow room air or other materials to move from outside the mask to inside the mask in some embodiments. A vent(s) may move air within the mask and in particular may move air within a reservoir of the mask. The mask may have a vent(s) on a midline of the mask, or on one or both sides of the midline. There may be a plurality of exhalation vents. There may be one, two, or more exhalation vents. In one example there may be 10 or more vents. A lateral sampling port may be located outside an area encompassed by the exhalation vents, as shown in FIGS. 1-3. A lateral sampling port may be located near an exhalation vent. A lateral sampling port may be located as close to one or more exhalation vents as possible, such as left sampling port 12 located near exhalation vents 16 as shown in FIG. 3. In one example, a lateral sampling port may be located about 1 mm away from an exhalation vent. In one example, the distance between a center of a lateral sampling port and a vent is about 15 mm. In another example, a distance between a center of a lateral sampling port and a center of the vents is about 15 mm.

A plurality of exhalation vents (e.g. perforations) may be arranged around a lateral sampling port. A plurality of vents may define a vent center 27, as shown on mask 10 in FIG. 1. A port 14 may be located at or near a vent center substantially surrounded by exhalation vents as shown in FIG. 1B. In another example, a sampling port is outside an area of the vents and a distance between a center of a sampling port and a center of the vents is about 15 mm.

The exhalation vents may have a point of attachment (e.g. a coupling point) 15 near or at the vent center as shown in FIGS. 2 and 3. A flexible diaphragm may be coupled with a point of attachment to create a one way valve (e.g. over the vent(s)), such as for use with a non-rebreather apparatus. The one way valve may allow gas inside the mask to move to outside the mask, while substantially not allowing gas outside the mask (e.g. room air) to move inside the mask.

The exhalation vents may be low resistance to air flow as air flows out of the exhalation holes; locating the lateral sampling ports near the exhalation vents may allow more accurate sampling of exhaled gas as the gas is moved past the lateral sampling port. If gas is sampled near the inflow stream of oxygen, the sampling accuracy may be lowered. This may especially be the case in high minute ventilation scenarios when carbon dioxide levels are low and/or oxygen flow rates are high.

Mask 10 may have reservoir 19 containing a pocket of gas (e.g. air) as shown in FIGS. 2 and 3. The reservoir may allow gas mixing and provide a space near nose 32 (e.g. near the nostrils) and mouth 30 to facilitate breathing. In one example, the reservoir may extend from a level near the mouth to a level near the nose when the mask is positioned on a user. In another example, the reservoir may extend to about the bottom of the nose when the mask is in use. In one example, the reservoir extends about 50 mm vertically, 50 mm horizontally, and 50 mm in the anterior posterior dimension. A sampling port may be located in the reservoir region of the mask. As shown in FIG. 3, left lateral port 12 exits the mask from reservoir 19.

Positioning a sampling ports away from the oxygen inlet port may make it easier (or even possible) for a care provider to change the oxygen conduit (e.g. tubing) leading to an oxygen inlet port or another connector which might not be possible if a sampling port (or conduit connected with a sampling port) is too close to the oxygen delivery port. For example, it may be easier to change a nebulizer device coupled with the oxygen inlet port without having a sampling port nearby obstructing access. The sampling ports may be positioned far enough away from an oxygen line connector to enable a care provider to attach both a sampling conduit and a specialized apparatus to the mask including a nebulizer, a nonrebreather, an oxygen calibration device (e.g. a Venturi device), or a high flow oxygen source.

A sampling port may have any shape or configuration that allows gas to move through and to connect with a conduit or sampling device. The port may be low profile or hardly visible. The sampling port may be e.g. circular, square, hexagonal, or slotted. The sampling port may have a mating part or fitting configured to removably connect with a different mating part or fitting on a conduit, including a sensing conduit. The mating part may be any as known in the art (e.g. threads, slots, pins, lock-and-key mechanism, etc.). In one example, a mating part on the sampling port is a Luer-lock that can couple with a Luer-lock on a sampling port conduit.

Any type of sampling conduit may be used. In one example, sampling conduit is a flexible polyurethane tubing. Sampling conduit may have a narrow diameter; the diameter may be smaller than a diameter of an oxygen conduit. In one example a sampling conduit may have about a ¼ inch inner diameter or ⅜ inch outer diameter.

Figure 4:
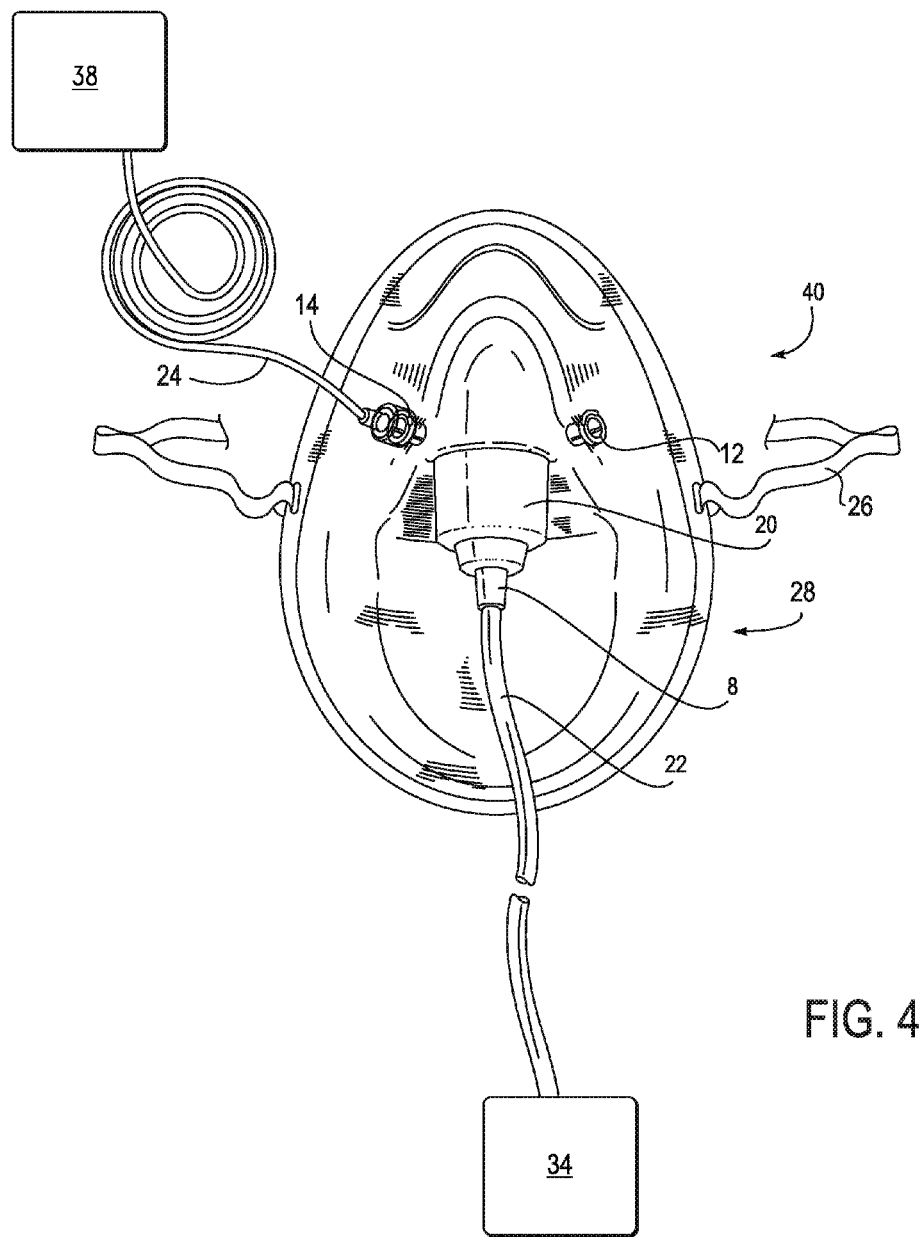
FIG. 4 shows a front view of a face mask with sampling conduit connected to one of the lateral sampling ports.

One method of using an oxygen face mask having two lateral sampling ports according to the current disclosure includes choosing a lateral sampling port and coupling a conduit with the port. FIG. 4 shows mask 28 with left, right lateral sampling ports 12, 14. Conduit 24 is connected with right lateral sampling port 14 to enable gas (e.g. carbon dioxide) sampling according to a method of the disclosure. The method may further include the step of obtaining a sample from the port. In one example obtaining the sample comprises obtaining a sample without an anesthetic in it (e.g. without an inhaled anesthetic). The method may include the step of coupling an expiratory gas sensor to the conduit; and the expiratory gas sensor may be configured to detect carbon dioxide. The method may include the step of analyzing the sample for a component. The method may include the step of analyzing carbon dioxide (e.g. a partial pressure of carbon dioxide). The method may include the steps of removing the sampling conduit, and reattaching the conduit. The method may include the steps of providing oxygen, venting an expiratory gas, and/or administering a nebulizer or aerosol agent or treatment.

In one example, the method includes providing at least about 21-100% oxygen. The range includes providing room air (e.g. about 21% oxygen) to providing pure oxygen (e.g. around 100% oxygen), such as deliverable by a nonrebreather or high flow device. In one particular embodiment, at least about 60% oxygen is provided. FIG. 4 depicts oxygen source 34 providing oxygen through oxygen conduit 22 to oxygen inlet port 20. The oxygen source can be any as known in the art (e.g. an oxygen tank or a bag connected to an oxygen tank). In one example, monitoring may be performed without providing supplemental oxygen (e.g. only providing room air).

Any material may be sampled from the port. Any characteristic of the material may be analyzed. Gas may be sampled from the port or a component present with the gas may be sampled. The gas may contain other components such a therapeutic nebulized or aerosolized component or agent. The gas may be expired gas. The expired gas may be mixed, in part, with delivered oxygen, and/or room air before sampling. In one example, the gas may not contain expired air (e.g. if the patient is not breathing). In one example, carbon dioxide is sampled (capnography). In another example, oxygen is sampled. In another example, end tidal partial pressure of the gas (e.g. carbon dioxide) may be measured.

Any device or means (e.g. sensor) may be used to sample a gas. FIG. 4 shows sensor 38 coupled with sampling conduit 24 for analyzing a sample from right sampling port 14. A sensor may be connected to a sampling conduit, or the conduit may be the sensor. Any characteristic of a gas may be sensed. An amount of a gas, a change in a level of a gas, and/or a change in a pressure of a gas may be sensed. A partial pressure of a gas may be assayed. In one example, carbon dioxide is measured and an infrared sensor is used (capnograph). In another case, carbon dioxide may be measured and a colorimetric sensor may be used (see, e.g. U.S. Pat. No. 5,857,460 to Popitz).

A system according to the disclosure may include a facemask and one or more components that can be used with the mask. The system may include a component configured to obtain, move, provide, sense, assay and/or measure a level of a gas. FIG. 4 shows system 40 with mask 28, sampling conduit 24, sensor 38, oxygen conduit 22, and oxygen source 34. The system may include a mask, a mask sealing agent, a face contact agent (e.g., a lotion), sampling conduit, oxygen conduit, an oxygen reservoir (e.g., partial or full rebreather reservoir), a one way valve or valve cover and/or an oxygen source (e.g., tank). In one particular example, the system includes a face mask and a sensor configured to detect a characteristic of a gas, such as a carbon dioxide partial pressure. The sensor may be coupled with or configured to be coupled with a lateral port.

Figure 6:
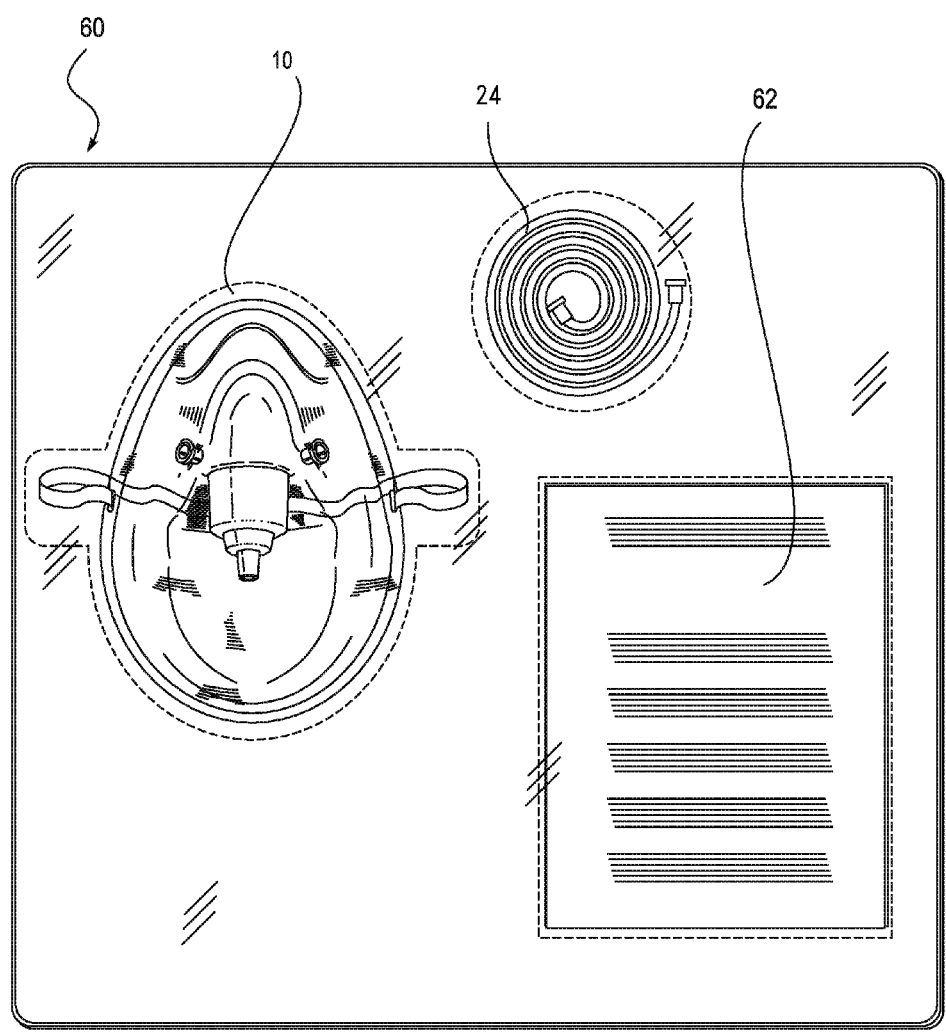
FIG. 6 shows a face mask kit according to one aspect of the disclosure.

The face mask may be packaged into a kit. A kit may have any component configured to be used with the face mask. The kit may include e.g. a face mask, a sampling conduit, a sensor, an oxygen conduit, a rebreather reservoir, a one way valve, and/or an instruction(s) for use. FIG. 6 shows kit 60 with facemask 10, sampling conduit 24, and instruction for use 62.

The facemask or facemask system or a component used with the facemask may include an alarm. The alarm may provide a signal in response to a result from a component measurement. The alarm may be any (e.g. visual, auditory). The alarm may provide a signal when a level of an expiratory gas is at or different from a threshold amount (e.g. is above or below a threshold amount). In one example, the alarm is auditory and provides a signal when a level of carbon dioxide is different from a threshold level (e.g. when a partial pressure of carbon dioxide is below a threshold level).

Any material can be delivered through the mask to the patient that would benefit the individual. Gas (e.g. room air, oxygen, and/or respired air) may be delivered. Room air, oxygen, and/or respired air may be delivered with or without also delivering an anesthetic agent and with or without a sample being monitored. Room air may be delivered through vents in the mask, through an oxygen line connector, through another connector, or along an unsealed or open edge of the mask. Room air may be mixed with another gas (e.g. oxygen) and delivered.

In one example, oxygen is delivered through the oxygen inlet port. The amount of oxygen delivered may be any therapeutic amount (e.g. 21-100%). The oxygen may be delivered at any flow (e.g. low, medium, or high flow).

The oxygen may be delivered at a relatively low flow rate. In another example, respired air may be delivered with oxygen. A reservoir or bag configured to supply oxygen and respired air may be coupled with the mask. The mask may have a one way valve on one or more exhalation vents to release expired air to the room (e.g. a rebreather or partial rebreather mask) without substantially allowing room air into the mask.

The oxygen may be delivered to the face mask with little or no exhaled air delivered or remaining in the face mask (e.g. the mask or mask system may be a non-rebreather or partial rebreather mask or mask system). An exhalation vent may include a one-way valve configured to allow the release of gas (e.g. exhaled air) from the mask without allowing intake of room air. In one example, oxygen may be delivered using a reservoir bag. The reservoir bag may be connected with the mask using an oxygen line connector or other connector and may be connected with a source of oxygen (e.g. an oxygen tank). The connection between the reservoir bag and the mask may include a one way valve that prevents inhaled air from entering the reservoir. Any of the components may be connected with the mask, or may be separate from the mask. A system including the oxygen mask of the disclosure may include one of more components for connecting with or using with the face mask.

The oxygen may be delivered at a relatively high flow or pressure (e.g. 4 to 10 L/min) into the mask (e.g. a Venturi mask). The high flow may in turn cause a percentage of the oxygen in the mask to be higher or controlled (e.g. more constant).

Alternatively, a device for creating or delivering a nebulized agent (e.g. a nebulizer) or aerosoled agent may be connected with the oxygen line connector or another connector. Any material may be delivered through a nebulizer device. For example, a bronchodilator or glucocorticoid may be delivered. In one example, albuterol is delivered. In another example, ipratropium may be delivered. This may be especially beneficial for a patient suffering from COPD or asthma.

The mask could instead have a single sampling port located along the midline of the oxygen mask. The sampling port may be located between the nose and the mouth. The sampling port may be located above and away from a mask component configured for delivering oxygen. A mask with a low profile sampling port at the midline may be easy to use and minimally obstructive to the patient's view. In one example, the opening of the sampling port may point downwards (e.g. away from the user's eyes).

The mask may be any shape that fits over a portion of the patient's face to provide oxygen and obtain a gas sample. The mask may be generally diamond shaped or may be oval. The mask may have features to accommodate contours of the face (e.g. the nose, chin, cheeks). Different masks may have features for different individuals (e.g. large patient, obese patient, pediatric patient). The facemask may be configured to cover the nose and mouth. The mask may cover the nose and part of the mouth. The mask may cover the nose and all of the mouth. The mask may be configured for use on a mammal (e.g. a human). The facemask may exclude covering the eyes.

Figure 5A:
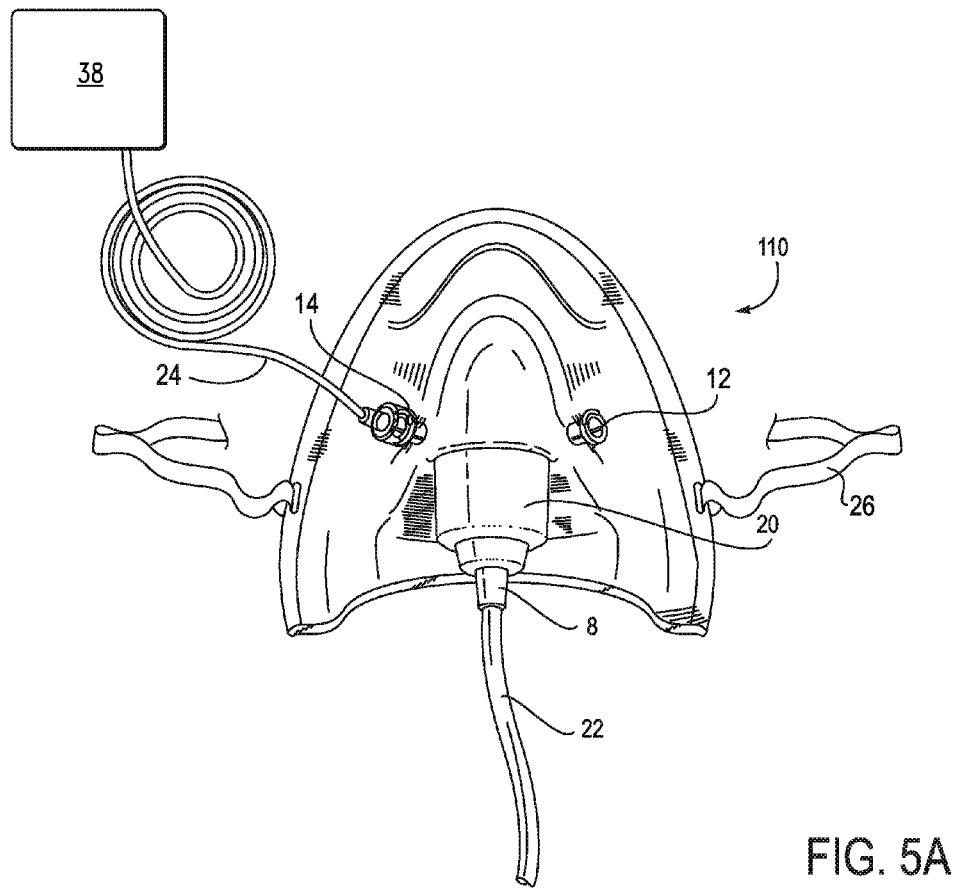
FIG. 5A shows a short facemask to allow access to an individual's mouth and face.
Figure 5B:
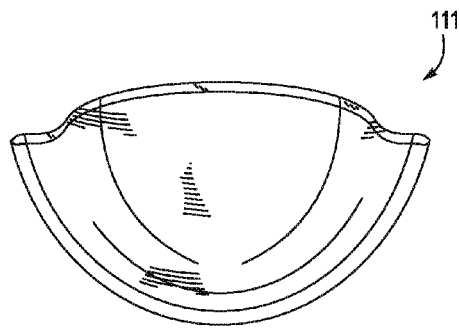
FIG. 5B shows a bottom portion of a facemask removed from a full mask to form the short mask shown in FIG. 5A, according to one aspect of the disclosure.

According to one embodiment, a mask with lateral sampling ports may be a short mask, having a top portion without a bottom portion. A short mask allows access to the lower part of the patient's face (e.g. a patient's mouth). FIG. 5A shows short face mask 110 with various features, including right and left lateral sampling ports 12, 14, straps 26, and oxygen inlet port 20. Right lateral sampling port 14 is connected with sensor 38 through conduit 24 for sampling an expiratory gas. Left lateral sampling port 12 is not being used in this example. A short mask may be directly manufactured, or may be made by cutting a full (e.g. long mask) to remove a bottom portion of the face mask. FIG. 5B shows a bottom portion 111 of a face mask that has been removed from a top portion, to create a face mask such as face mask 110 of FIG. 5A.

In another embodiment, a mask may not have exhalation ports. For example, a mask open at the bottom, such as a short mask shown in FIG. 5 might not need exhalation ports. Prior art masks having a sampling port closer to the bottom of the mask are cumbersome to use in procedures in which the bottom part of the mask may be removed but where expiratory gases still need to be measured. Access to the lower part of the patient's face may be for any reason. A short mask may allow an endotracheal tube, endoscope, or echocardiogram probe to be inserted into the patient's mouth. The endotracheal tube may provide oxygen and anesthesia to the patient. In one example, access to the patient's mouth may allow nourishment or fluids to be provided. In another example, access may allow a procedure to be formed, such as a facial procedure or surgery or dental work.

The mask may be any size to fit an individual. In one example, the mask may be configured to fit onto most average adults. The mask may be configured to fit an especially large or obese individual (e.g. may be larger or may have a different shape). In another example, the mask may be configured to fit a child. In another example, the mask may be configured to fit a baby.

The mask may have a sealing portion to removably seal or connect with the user's face. The sealing portion may retain gas in the mask; the sealing portion may reduce or prevent expiratory gas and/or oxygen from escaping from the mask. The sealing portion may be an edge portion of the mask. The mask may have special features (e.g. silicone edges, a sealing air pocket, lubricant, etc.) to improve the connection or removal of the mask relative to the face or to make the mask more comfortable when in use.

The mask may have any type of fastener or holder to hold the mask in place (e.g. an elastic loop to go behind the head, loops to go around the ears, etc.).

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A face mask to cover a user's nose and at least partially cover a user's mouth and configured to deliver oxygen to a user, the face mask comprising:
   a reservoir adapted to contain a pocket of gas;
   an inlet port configured to deliver gas to the reservoir;
   a first lateral sampling port at the center of the first vent and a second lateral sampling port at the center of the second vent, each of the first and second sampling ports extending through the mask to be in fluid communication with the reservoir and configured to sample the pocket of gas within the reservoir; and
   a connector on at least one of the first and second lateral sampling ports, the connector configured to connect to a conduit.

2. The face mask of claim 1 further comprising the conduit coupled to the first sampling port wherein the second sampling port is not coupled with the conduit during normal face mask use.

3. The face mask of claim 1 wherein each of the first and second vents comprises a plurality of vent openings surrounding the respective first and second sampling ports.

4. The face mask of claim 1 further comprising a portion configured to removably connect with a user's face to thereby create a mask sealing portion configured to retain gas in the mask.

5. A breathing mask system comprising a face mask configured to cover a user's nose and at least partially cover a user's mouth, the face mask comprising:
   a reservoir adapted to contain a pocket of gas;
   an inlet port configured to deliver gas to the reservoir;
   first and second lateral sampling ports on opposing sides of a midline of the mask;
   first and second configured to provide gas flow through the mask and to release gas from the reservoir, the first lateral sampling port at a center of the first vent, the second lateral sampling port at a center of the second vent, the first and second lateral sampling ports configured to sample an expiratory gas from the reservoir; and
   a sensor coupled to the first lateral sampling port, the sensor configured to detect the expiratory gas.

6. The system of claim 5 further comprising an alarm configured to provide a signal when a level of an expiratory gas detected by the sensor is different from a threshold amount.

7. The system of claim 5 wherein the sensor is configured to detect a carbon dioxide pressure.

8. The system of claim 5, the face mask further comprising an oxygen inlet port.

* * * * *

UNITED STATES PATENT AND TRADEMARK OFFICE
CERTIFICATE OF CORRECTION

| | | |
|---|---|---|
| PATENT NO. | : 9,138,169 B2 | Page 1 of 1 |
| APPLICATION NO. | : 13/227345 | |
| DATED | : September 22, 2015 | |
| INVENTOR(S) | : Beard | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 401 days.

In the Claims:

Column 10, Lines 26-27:
"an inlet port configured to deliver gas to the reservoir;
a first lateral sampling port at the center of the first vent and"
should read,
--an inlet port configured to deliver gas to the reservoir;
first and second vents on opposite sides of a midline of the mask and configured to vent gas from the reservoir through the mask, each vent having a center;
a first lateral sampling port at the center of the first vent and--.

Column 10, Line 54:
"first and second configured to provide gas flow through the" should read, --first and second vents configured to provide gas flow through the--.

Signed and Sealed this
Twenty-fourth Day of May, 2016

Michelle K. Lee
*Director of the United States Patent and Trademark Office*